United States Patent [19]
Best et al.

[11] Patent Number: 5,151,090
[45] Date of Patent: Sep. 29, 1992

[54] SYRINGE AND NEEDLE GUARD ASSEMBLY

[75] Inventors: Robert J. Best, Winthrop Harbor; Mark E. Larkin, Lindenhurst; Juergen H. Zaha, Winthrop Harbor, all of Ill.

[73] Assignee: Abbott Laboratories, Abbott Park, Ill.

[21] Appl. No.: 600,556

[22] Filed: Oct. 19, 1990

[51] Int. Cl.5 ............................................. A61M 5/32
[52] U.S. Cl. ..................................... 604/192; 604/86; 604/263
[58] Field of Search ................ 604/192, 198, 110, 82, 604/83, 86-88, 263, 283, 284, 905

[56] References Cited

U.S. PATENT DOCUMENTS

| | | | |
|---|---|---|---|
| 4,083,370 | 4/1978 | Taylor | 604/117 X |
| 4,747,835 | 5/1988 | Sandhaus | 604/192 |
| 4,810,248 | 3/1989 | Masters et al. | 604/192 |
| 4,834,716 | 5/1989 | Ogle, II | 604/192 |
| 4,946,445 | 8/1990 | Lynn | 604/192 |
| 4,964,855 | 10/1990 | Todd et al. | 604/283 |
| 4,998,713 | 3/1991 | Vaillancourt | 604/283 |
| 4,998,922 | 3/1991 | Kuracina et al. | 604/192 |
| 5,011,475 | 4/1991 | Olson | 604/192 |
| 5,084,032 | 1/1992 | Kornberg et al. | 604/263 |
| 5,088,985 | 2/1992 | Deras | 604/192 |

FOREIGN PATENT DOCUMENTS 8910770 11/1989 PCT Int'l Appl. ................ 604/192

Primary Examiner—John D. Yasko
Assistant Examiner—Adam J. Cermak
Attorney, Agent, or Firm—A. Nicholas Trausch; Clifford A. Dean

[57] ABSTRACT

A needle guard for an additive-type syringe includes a sidewall which extends beyond the needle point. The sidewall is joined to the syringe housing by spin welding or sonic welding an annular flange that extends axially rearward from the needle guard to contact the front wall of the housing. The needle guard also includes an intermediate circumferential flange and a centering and guiding member that frictionally slides in the needle guard.

12 Claims, 1 Drawing Sheet

SYRINGE AND NEEDLE GUARD ASSEMBLY

BACKGROUND OF THE INVENTION

The present invention relates to a syringe for introducing a solution into an I.V. administration line or into an I.V. solution container and in particular to a needle guard for an additive-type syringe.

Drugs and other medical solutions are commonly administered to patients intravenously through an intravenous administration set. A primary I.V. solution flows from an I.V. solution container through a tube to a needle positioned within a vein of the patient. I.V. administration sets are typically provided with Y-injection sites so that a second I.V. solution can be administered through the same needle. The Y site is commonly used for bolus or additive injections of drugs from a syringe such as the Abboject ® syringe sold by Abbott Laboratories. The Abboject syringe consists of a calibrated glass vial prefilled with a medical solution. A matching vial injector includes an integral syringe needle for injecting the solution into a reseal septum of the Y site, for example.

It is desirable to protect the syringe needle from breaking and contamination and also to protect the health care worker from accidental needle stick. One example of a protective sheath for a syringe needle is shown in Nitshke U.S. Pat. No. 4,232,669. It is noted, however, that the sheath of Nitshke does not extend beyond the needle point, thus exposing the health care worker to potential needle stick. Also, the sheath design does not allow the syringe to be used in a piggy-back fashion with a Y site of an I.V. administration set.

Another example of a protected cannula is disclosed in Ogle U.S. Pat. No. 4,834,716. The protective sheath of the Ogle combination is fixed to the needle boss of the syringe. However, fixing the sheath to the small diameter needle boss does not provide any additional structural support to protect the needle boss from breaking.

It is therefore an object of the present invention to provide an improved needle guard for syringes used to inject secondary fluids into I.V. administration sets so as to reduce the risk of accidental needle stick to the health care provider.

It is an important object of the present invention to provide a needle guard to protect the needle and needle hub from breaking.

It is another object of the invention to provide an indication whether the syringe has been used.

It is a further object of the present invention to assure that the point of the syringe needle enters the center of the additive septum so as to prevent skivvying of the needle point into the reseal retaining wall.

SUMMARY OF THE INVENTION

The present invention is directed to an additive-type syringe that includes a needle guard mounted on the syringe housing.

More particularly the needle guard includes a cylindrical sidewall which extends beyond the pointed end of the syringe needle. An internal circumferential flange at an intermediate position in the sidewall defines an opening sized to receive the needle hub. An annular flange extends axially rearward from the needle guard to contact the front wall of the syringe housing. The axial flange is used to join the needle guard to the housing by either a spin welding or sonic welding assembly process.

The needle guard may also include a sliding member which centers the syringe needle in the sidewall and guides the center of a reseal member into piercing contact with the needle.

Cut-outs are provided in the sidewall to accommodate different configurations of reseal members.

Other advantages and features of the present invention will become apparent from the following detailed description, the accompanying drawings and the appended claims.

DETAILED DESCRIPTION OF THE PREFERRED EMBODIMENT

Figure 1:
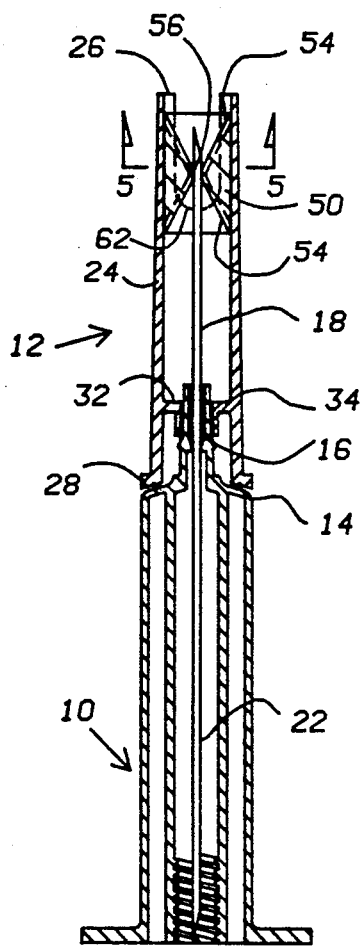
FIG. 1 is a cross section of one embodiment of the present invention showing the needle guard assembly before use.

FIG. 1 shows an embodiment of the present invention including a syringe housing 10 and a needle guard assembly 12 located at the forward end of the housing. In the following description, front and forward refers to the direction that the sharp end of the syringe needle is pointing, i.e., up in FIG. 1; rear and backward refers to the direction away from the sharp end, i.e. down in FIG. 1. The syringe housing 10 is an elongated hollow cylinder typically constructed of a molded plastic. The housing has an open end and a substantially closed end. Front wall portion 14 substantially closes the front end of the syringe housing. An integrally molded needle hub 16 extends forward from the front wall and secures a needle cannula 18. The needle extends forward from the hub and terminates with a sharp needle point 20.

A glass vial (not shown) is prefilled with a solution and sealed with a stopper. The vial and stopper engage the open end to the syringe housing and the rear portion 22 of the needle cannula in a well known manner so as to provide fluid communication with the needle cannula.

The needle guard assembly 12 is coaxially mounted on the front wall portion 14 of the syringe housing. The needle guard 12 is an independently molded hollow cylinder having a cylindrical sidewall 24 longitudinally extending forward beyond the needle point of the cannula. The sidewall has an open end 26 at the front of the cylindrical sidewall and a second end 28 at the rear of the sidewall that abuts the front wall portion 14 of the syringe housing. The needle guard 12 is mounted on the syringe housing 10 by various configurations and assembly processes that will be described.

The needle guard further includes a circumferential flange 32 extending radially inward from the sidewall and partially closing the hollow cylinder at an intermediate point between the front open end and the second end of the cylindrical sidewall. The circumferential flange 32 defines an opening 34 sized to receive the needle hub 16 with a loose slip fit. The fit of the hub in the opening 34 helps position the needle guide in general coaxial alignment with the syringe housing.

Figure 3:
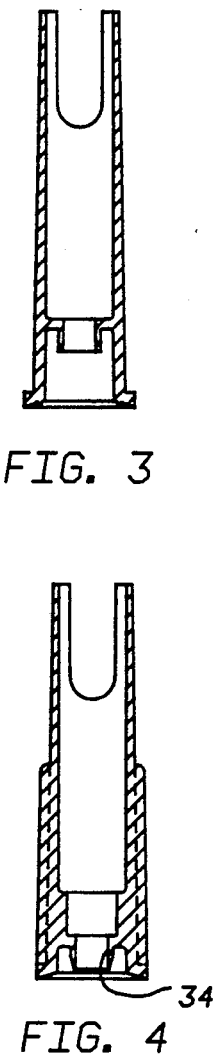
FIG. 3 is a schematic of the present invention showing a first arrangement for joining the needle guard to the syringe housing.
Figure 4:
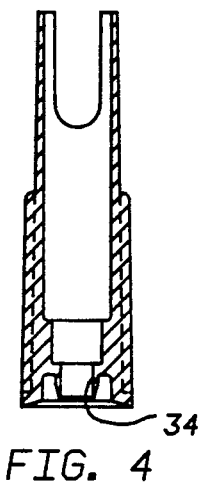
FIG. 4 is an alternate arrangement for joining the needle guard to the syringe housing.

Referring now to the embodiment of FIGS. 3 and 4, an annular member is provided on the needle guard that extends axially rearward from the needle guard for joining the needle guard assembly 12 to the front wall 14 of the syringe housing.

Figure 6:
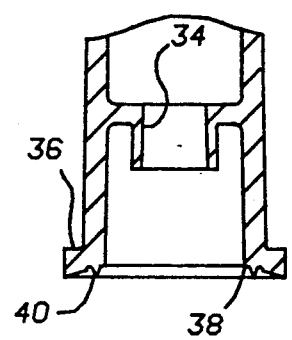
FIG. 6 is an enlarged portion of FIG. 3.

As shown in FIG. 3 and 6, a radially outward extending base 36 is provided at the second end of the sidewall. The rear face 38 of the base is adapted to have a parallel configuration with the front wall portion 14 of the syringe housing such that when the housing and the needle guard are joined during the assembly process, the radial base abuts the front wall of the syringe. As best seen in FIG. 6, the annular joining member 40 extends axially rearward from the rear face of base member 36.

When a spin welding assembly process is used to join the needle guard to the syringe housing, the annular joining member is configured in a conventional manner as a small fusible flange that extends from the radial base so as to contact the front wall of the syringe when the hub 16 is received in the opening 34. The needle guard is then joined to the syringe housing by spin welding the guard to the housing. Alternatively when a sonic welding assembly process is used to join the needle guard to the syringe housing the annular joining member 40 is constructed in a conventional manner as a sonic energy concentrating flange. The concentrating flange extends from the radial base 38 so as to contact the front wall of the housing when hub 16 is received in opening 34. The needle guard and syringe housing are joined by sonic welding. In both of the above assembly processes, the radial base member 38 allows the assembly machinery to provide axial pressure so as to keep the needle guard and syringe housing in axial contact during the joining process.

Figure 7:
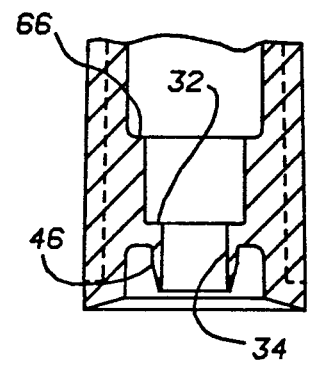
FIG. 7 is an enlarged portion of FIG. 4.

In the embodiment shown in FIGS. 4 and 7, the annular joining member is an annular flange 46 that axially extends from the circumferential flange 32 at a position radially inward from and coaxial with the sidewall 24. The annular flange 46 extends so as to contact the front wall 14 of the syringe housing when hub 16 is received in opening 34. The opening 34 through flange 46 also receives hub 16 with a loose slip fit. The needle guard and housing are joined by either the spin welding or sonic welding processes previously described.

Figure 5:
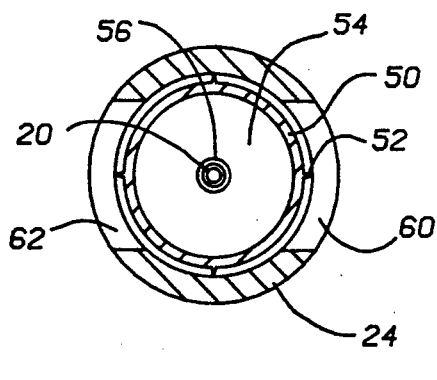
FIG. 5 is an enlarged cross-section at 5—5 of FIG. 1.

Referring now to FIGS. 1 and 5, additional features of the present invention will now be described. A centering guide 50 is shown positioned in the forward portion of the sidewall 24 of the needle guard. The centering guide 50 is an elongated, generally cylindrical member having an outer diameter slightly less than the inner diameter of the sidewall. The guide 50 is preferably symmetric and has an hourglass shape such as formed by two joined cones. Alternatively the guide may be cylindrical. Small longitudinally extending ribs 52 are equally spaced on the outer surface of the centering guide. The ribs are flexible and sized such that they provide a slight interference fit for the centering guide in the sidewall of the needle guard. Thus the centering guide 50 will remain in position unless it is pushed backward by an externally inserted member such as a Y-site for example. The centering guide has at least one conically tapering seat 54 on its interior surface. At the center of the seat is an orifice 56 sized such that it receives the needle 18 with clearance.

Figure 2:
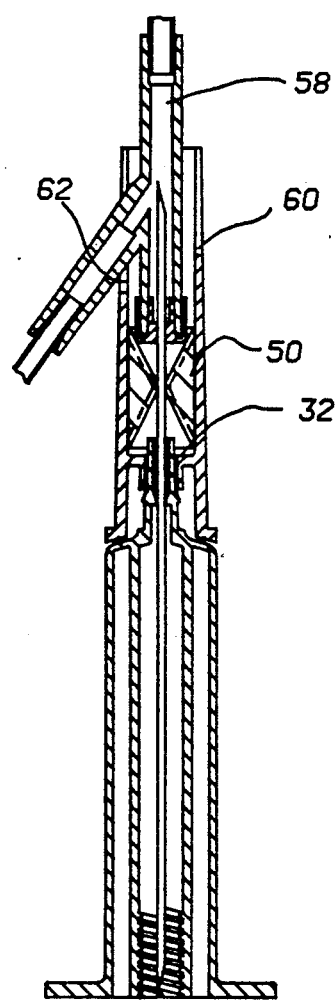
FIG. 2 is a cross section similar to FIG. 1 (turned 90°) showing the needle guard assembly in use with a Y-site.

Referring now to FIG. 2, the needle guard assembly is shown inserted onto a Y-site 58. A shallow cutout 60 and a deep cutout 62 are shown extending into the sidewall from the open end 26 of the guard. The two cutouts are positioned 180 degrees from each other. The different depths of the cutouts accommodate different configurations of Y-sites.

When an additive injection with the syringe and needle guard assembly of the present invention is made into a Y site of an I.V. line or into an additive port of an I.V. solution container, the open end 26 of the needle guard sidewall is positioned over the Y site reseal. As the syringe needle is pushed forward, the conically tapering seat 54 of the centering guide 50 guides the center of the reseal into contact with the needle point, thus preventing skivvying of the needle point into the reseal retaining wall. As the syringe assembly is pushed further on to the Y site, the centering guide 50 is pushed rearward in the needle guard. As shown in FIG. 2, the backward movement of the centering guide is limited by the circumferential flange 32 or by a step 66 in FIG. 7, which limits the depth the needle 18 can penetrate into the reseal.

After the drug contained in the syringe has been injected into the I.V. set, the syringe assembly is disengaged from the Y site reseal. The centering guide 50 remains in the rear position as shown in FIG. 2 and is no longer visible at the front end of the needle guard to the health care worker, indicating that the syringe has been used.

It will be apparent from the foregoing description that the needle guard of the present invention not only protects the health care user from inadvertent or accidental needle stick, but also provides additional advantages. Both the needle and the needle hub are protected from being broken off by the needle guard which is securely attached to the syringe housing. The sliding centering guide assures proper centering of the needle into the reseal of the Y site or I.V. container. The centering device also controls the depth of needle insertion into the Y site and its position indicates if the syringe has been used.

Although the present invention has been disclosed in terms of a preferred embodiment, it will be apparent to those skilled in the art that variations and modifications can be made without departing from the spirit and scope of the invention as defined in the following claims.

I claim:

1. An additive-type syringe and needle guard assembly including a syringe housing having a front wall substantially closing one end of the housing and a needle hub extending forward from said front wall for securing a needle cannula, said needle cannula extending forward from the hub and terminating with a needle point, and a needle guard fixedly mounted coaxially with the needle hub on said front wall of the syringe housing to protect the needle cannula during use of the assembly in injecting fluids into I.V. administration sets including Y-sites, the syringe and needle guard assembly comprising:

an outwardly flared surface defined by said front wall of said syringe housing;

an elongated member defining said needle guard and having a cylindrical side wall extending forward beyond the needle point of the cannula a fixed distance and having a first open end at the front of the cylindrical side wall and a second outwardly flared open end at the rear of the cylindrical side wall and adjacent said outwardly flared surface defined by said front wall of said syringe housing;

a circumferential flange disposed on and within said elongated member inwardly of the sidewall and intermediate the first open end and the second end of the cylindrical sidewall, said circumferential flange defining an open sized for said needle hub; and annular means disposed between said adjacent flared surfaces and joining the needle guard to the front wall of the syringe housing.

2. The syringe and needle guard assembly of claim 1 wherein the annular means is a spin-welded annular flange.

3. The syringe and needle guard assembly of claim 1 wherein the annular means is a sonic welded annular flange.

4. The syringe and needle guard assembly of claim 1 wherein the annular means extends from the circumferential flange.

5. The syringe and needle guard assembly of claim 4 wherein the annular means is a spin welded annular flange.

6. The syringe and needle guard assembly of claim 4 wherein the annular means is a sonic welded annular flange.

7. The syringe and needle guard assembly of claim 1 further comprising means for maintaining the needle point in the center of the needle guard and for guiding an inserted member into a center piercing contact with the needle point, said maintaining and guiding means being movable relative to said needle guard.

8. The syringe and needle guard assembly of claim 7 wherein the means for centering and guiding comprises a generally cylindrical member adapted to frictionally slide within the sidewall and having a center orifice adapted to receive the needle point and a conically tapered seat to guide the inserted member.

9. The syringe and needle guard assembly of claim 8 wherein the cylindrical member includes means to frictionally engage the sidewall.

10. The syringe and needle guard assembly of claim 9 wherein the cylindrical member is initially positioned at the first end of the sidewall and frictionally slides toward the second end only when pushed by an inserted member.

11. The syringe and needle guard assembly of claim 10 wherein the first open end of the sidewall has at least one cutout adapted to receive the inserted member.

12. The syringe and needle guard assembly of claim 10 wherein the first open end of the sidewall has a first shallow cutout and an oppositely disposed second deep cutout.

* * * * *